United States Patent
Enciso Ramos et al.

(10) Patent No.: US 12,325,680 B2
(45) Date of Patent: Jun. 10, 2025

(54) SYSTEM FOR METHANOL PRODUCTION FROM A SYNTHESIS GAS RICH IN HYDROGEN AND CO$_2$/CO

(71) Applicant: SENER, INGENIERIA Y SISTEMAS, S.A., Gexto-Vizcaya (ES)

(72) Inventors: Laura Enciso Ramos, Gexto-Vizcaya (ES); Sara Rodriguez Alonso, Gexto-Vizcaya (ES); Javier Llabrres Veguillas, Gexto-Vizcaya (ES)

(73) Assignee: SENER, INGENIERIA Y SISTEMAS, S.A., Gexto-Vizcaya (ES)

( * ) Notice: Subject to any disclaimer, the term of this patent is extended or adjusted under 35 U.S.C. 154(b) by 564 days.

(21) Appl. No.: 17/787,163

(22) PCT Filed: Dec. 15, 2020

(86) PCT No.: PCT/EP2020/086306
§ 371 (c)(1),
(2) Date: Jun. 17, 2022

(87) PCT Pub. No.: WO2021/122658
PCT Pub. Date: Jun. 24, 2021

(65) Prior Publication Data
US 2023/0031590 A1 Feb. 2, 2023

(30) Foreign Application Priority Data

Dec. 20, 2019 (EP) ..................................... 19218461

(51) Int. Cl.
*C07C 29/152* (2006.01)
*B01J 4/00* (2006.01)
*B01J 8/04* (2006.01)

(52) U.S. Cl.
CPC ............... *C07C 29/152* (2013.01); *B01J 8/04* (2013.01); *B01J 4/002* (2013.01); *B01J 2208/0084* (2013.01); *B01J 2208/00902* (2013.01)

(58) Field of Classification Search
CPC ........ C07C 29/1516; C07C 31/04; B01J 8/04; B01J 4/002; B01J 2208/0084;
(Continued)

(56) References Cited

U.S. PATENT DOCUMENTS

| | | | |
|---|---|---|---|
| 3,475,136 A | 10/1969 | Eschenbrenner et al. | |
| 4,411,877 A * | 10/1983 | Notman | C07C 29/1518 518/713 |

(Continued)

FOREIGN PATENT DOCUMENTS

| | | |
|---|---|---|
| EP | 0026057 A1 | 4/1981 |
| EP | 0359952 A2 | 3/1990 |
| EP | 0448019 A2 | 9/1991 |
| EP | 0483919 A2 | 5/1992 |
| EP | 0988267 B1 | 10/2003 |
| EP | 1903002 A2 | 3/2008 |
| EP | 2626129 A1 | 8/2013 |

(Continued)

OTHER PUBLICATIONS

International Search Report and Written Opinion for Corresponding International Application No. PCT/EP2020/086306 (16 Pages) (Apr. 14, 2021).

*Primary Examiner* — Jafar F Parsa
(74) *Attorney, Agent, or Firm* — LUCAS & MERCANTI, LLP

(57) ABSTRACT

A system for methanol synthesis from a synthesis gas rich in hydrogen and CO2/CO having a first adiabatic reactor (11) with a structure having an inlet stream (10), a first catalytic bed (12), one Venturi type mixing element (13), a first divergent nozzle (14), a second catalytic bed (27) and one outlet stream (28) all of them connected sequentially to each other; a first heat exchanger (15) connected to the outlet stream (28) downstream the reactor (11); a condenser (16) connected to the heat exchanger (15) downstream of the heat exchanger (15); a separator (18) connected to the condenser (16); a first cold gas stream (19) joining the separator (18) to both the first heat exchanger (15) and the first Venturi type mixing element (13); a first outlet stream (21) joining the (Continued)

heat exchanger (15) to a second adiabatic reactor (24) similar to the first adiabatic reactor (11).

5 Claims, 5 Drawing Sheets

(58) Field of Classification Search
CPC .......... B01J 2208/00902; B01J 2204/00; B01J 8/0457; B01J 8/0492; B01J 8/0453
See application file for complete search history.

(56) References Cited

U.S. PATENT DOCUMENTS

| | | | |
|---|---|---|---|
| 5,173,513 | A | 12/1992 | Pinto |
| 5,216,034 | A | 6/1993 | Sie |
| 5,262,443 | A | 11/1993 | Topsoe et al. |
| 6,881,759 | B2 | 4/2005 | Nielsen et al. |
| 8,629,190 | B2 | 1/2014 | Kopetsch |
| 2011/0081282 | A1 | 4/2011 | Parimi et al. |
| 2018/0237366 | A1* | 8/2018 | Modarresi ............... C07C 29/15 |

FOREIGN PATENT DOCUMENTS

| | | |
|---|---|---|
| MX | 2015000667 A | 4/2015 |
| WO | 2004065341 A1 | 8/2004 |
| WO | 2017025272 A1 | 2/2017 |

* cited by examiner

SYSTEM FOR METHANOL PRODUCTION FROM A SYNTHESIS GAS RICH IN HYDROGEN AND $CO_2/CO$

CROSS-REFERENCE TO RELATED APPLICATIONS

This application is a 371 of PCT/EP2020/086306, filed Dec. 15, 2020, which claims the benefit of European Patent Application No. 19218461.2, filed Dec. 20, 2019, each of which are incorporated herein by reference.

FIELD OF THE INVENTION

The field of the invention relates to methanol synthesis, in which the reagents are hydrogen and $CO_2$, with or without CO, depending on its origin.

BACKGROUND ART

Methanol is a key chemical basic product. It has many uses. Could be used in mobility (liquid fuel) directly or via production of MTBE and DME. It is also used to produce chemicals as acetic acid and formaldehyde, which are used in products like polymers such as adhesives, foams, etc. Other applications are producing solvents and in polygeneration (power, heat, cold). The methanol-to-olefins process is also generating more and more interest nowadays.

Methanol is produced from synthesis gas (syngas) that is a gas mixture consisting primarily of hydrogen (H2), carbon monoxide (CO) and carbon dioxide (CO2). The most extended process used to generate said syngas is by steam reforming of natural gas. Other alternative processes to generate the syngas are based on the gasification of carbonaceous materials (biomass, fossil fuels, etc.). Another alternative process to generate the syngas is based on mixing the hydrogen produced from renewable electrical energy by using electrolysers that split water into hydrogen and oxygen, with the carbon dioxide captured from industrial processes.

The syngas rich in $H_2$ and $CO_2/CO$ may then be sent to a reactor for methanol synthesis. The main reactions are equilibrium exothermic type:

1. Methanol Synthesis from $CO_2$

$$CO_2 + 3H_2 \leftrightarrow CH_3OH + H_2O \quad \text{(Light Exothermic Reaction)}$$

2. Methanol Synthesis from CO

$$CO + 2H_2 \leftrightarrow CH_3OH \quad \text{(Moderate Exothermic Reaction)}$$

3. Water Gas Shift

$$CO + H_2O \rightarrow CO_2 + H_2 \quad \text{(Light Exothermic Reaction)}$$

These reactions require the use of a catalyst contained inside a reactor and given that reactions are exothermic, the reactor needs to be refrigerated.

The main limitation of the process of methanol synthesis is that the equilibrium conversion of $CO_2$ or CO is limited by pressure and temperature. According to the Le Chatelier principle, the higher the pressure the better is the equilibrium conversion to methanol, as shown in FIG. 1, for both CO and $CO_2$. Also, as the reactions are exothermic, lower operating temperatures will favour also the equilibrium conversion. The main problem is that operating at low temperature will affect also the reaction kinetics.

Normally in the commercial equipment operating temperatures between 200 and 300° C. are used. Also, the pressure is normally kept between 50-100 barg, which represents an optimum between equipment cost and conversion performance.

The alternatives to maximize the conversion and overcome this thermodynamic limitation hence the production of methanol have been the following:

a) Lowering the temperature of reaction. Although this is positive for the thermodynamics, there is a limit from which the reactions kinetics is affected, so the catalyst should be very active or the reactor too big, because of the residence time, so the cost of inversion would increase too much.

b) Recycling the unreacted reagents ($H_2$ and $CO/CO_2$). The global conversion to methanol increases but the problem is that the cost of investment and operation increases hence a big quantity of unreacted reagents require much bigger equipment and pipelines due to the volumetric flowrate increase (about 4/5 times). Despite these factors, this is the alternative used in the conventional process.

The conventional process of methanol synthesis consists on a reaction loop with a reactor refrigerated by means of boiling water inside. The compressed syngas enters in a reactor flowing downwards inside the reactor tubes filled with a catalyst. The exothermic reactions, that take place inside the catalyst, generate heat which is removed via steam generation in the shell side of the reactor.

Water from a steam drum enters the shell side and vaporizes. Vaporization of water into steam is an excellent medium to absorb heat with high heat transfer coefficients.

The reaction products exit the reactor and are conducted to a heat exchanger where are cooled down. Further cooling of the gas is performed in a condenser where the liquid products are obtained (mainly methanol and water). The liquid products and the unreacted gas are separated in a separator. A liquid stream named crude methanol is sent to a downstream separation unit with distillation operations to obtain high purity methanol. The unreacted gases are recycled again using a recycle gas compressor to the reactor to increase the overall reagents conversion. The recycle gas is normally between 4-5 times the net inlet flow. A purge is necessary to avoid inert gas accumulation in the reaction loop.

Different systems for methanol synthesis have been disclosed in the prior art.

U.S. Pat. No. 8,629,190B2 discloses a system for methanol production from a synthesis gas (containing hydrogen and carbon oxides) that is passed through a first water cooled reactor for producing methanol, the reaction products are guided to a gas/gas heat exchanger and then to an air/water condenser. The methanol product is separated, and the remaining synthesis gas is sent to a second reactor (gas cooled). It heats the inlet stream to the first reactor and produces more methanol which is further cooled, separated and the remaining synthesis gas is recycled to the first reactor using a recycle compressor.

EP0483919A2 describes a process characterised in that a gaseous mixture comprising hydrogen and carbon monoxide is reacted in the presence of a catalyst in a plurality of sequentially arranged stages. The gaseous mixture contacting the catalyst in each stage in a fluidized bed regime whilst being cooled, in which process methanol is removed from the reaction mixture between successive stages. The interstage removal of methanol is preferably carried out by cooling the effluent stream from the preceding reactor and allowing condensation of the methanol to occur. Cooling of the effluent stream is prefer-ably effected by heat exchange with cold feed gas, more preferably using a heat exchanger having a specific heat transfer area of at least 150 m²/m³, preferably of at least 200 m²/m³.

U.S. Pat. No. 5,216,034A discloses a similar system and a process for the production of methanol by reacting a gaseous mixture comprising hydrogen and carbon monoxide in the presence of a catalyst composition in a fluidized bed while cooling, characterized in that the reaction is carried out in a plurality of fluidized catalyst bed reactors in series with interstage removal of methanol from the reaction mixture.

Other example is U.S. Pat. No. 5,262,443A. The document discloses a method of preparing methanol by reacting synthesis gas comprising hydrogen and carbon oxides in a fixed bed of methanol synthesis catalyst. The reaction of the synthesis gas is conducted under conditions where condensation of methanol occurs on the catalyst. Pressure, temperature and/or space velocity of the gas at the exit of the catalyst bed are adjusted to where conversion levels of the gas leads to formation of liquid methanol in the catalyst bed by exceeding the dew point of the reaction mixture.

U.S. Pat. No. 6,881,759B2 describes a process for methanol production in a liquid phase reactor from a synthesis gas. The liquid phase reactor contains a solid catalyst suspended in methanol. The methanol acts both as a product and as a suspension medium for the catalyst. It exploits the condensing conditions for methanol production. By operating at condensing conditions, the methanol partial pressure at equilibrium is higher than the boiling pressure of methanol at the given temperature.

EP2626129A1 discloses a multiple reaction set for the production of chemicals by equilibrium limited reactions utilizing plate-type or extended surface heat ex-changers. The heat exchangers effectively cool the reaction products in order to condense the methanol contained within the reaction products for separation, and also to warm incoming feed reactants prior to entrance of the reactants into a reactor utilized for the production of methanol. The multiple reaction set can also be used for the recovery of methanol from a waste or purge gas stream utilizing multiple reactors, multiple plate-type or extended surface heat exchangers and multiple separators as a substitute for or in conjunction with a conventional methanol synthesis loop.

EP0988267B1 discloses a process for the production of methanol comprising converting a hydrocarbon feedstock at a pressure in the range 40 to 100 bar abs into a synthesis gas mixture containing hydrogen, carbon oxides and steam at an elevated temperature and pressure, cooling said mixture to condense water from the mixture, separating the condensed water, and passing the resultant gas mixture, with no further compression and no recycle of unreacted gas, at an elevated temperature through a series of at least two methanol synthesis stages with separation of synthesised methanol from the gas mixture after each stage.

The hydrocarbon feedstock is converted into the synthesis gas mixture by a catalytic steam reforming process wherein the heat required for reforming is supplied by the products of combustion of the unreacted gas remaining after separation of synthesised methanol, and, preferably also by the reformed gas after it has left the reforming catalyst.

WO2017025272 discloses a system focused in treating a low-quality synthesis gas, with impurities like chlorine or sulphur, that are known poisons for the methanol synthesis catalyst. To overcome this situations, one or two guard beds (adiabatic) are placed in the inlet to take care of such impurities. These guard beds also provide catalytic activity in methanol synthesis. Synthesis gases rich in CO will produce very high temperature (over 300° C.) in this bed as the result of exothermic methanol synthesis reactions. Temperatures over 300° C. on commercial catalyst will produce deactivation and will reduce the selectivity towards methanol. The patent focuses on an adequate temperature control to avoid this. The adiabatic bed is sub-sized at nominal load to limit the reaction extent and thus the temperature. In case of operating at partial load a controlled recycle is envisaged to control the reaction time and the maximum outlet bed temperature.

U.S. Pat. No. 5,173,513 discloses a system with a deficient hydrogen synthesis gas. It is mixed with a hydrogen rich gas and fed to a synthesis loop where it is mixed with unreacted gas from the synthesis stage. A part of this stream is taken from the loop. Either that part stream, or the gas in the loop prior to synthesis, is subjected to the catalytic shift reaction with steam. Carbon dioxide is removed from the gas taken from the loop to form the hydrogen rich stream.

MX 2015000667 A discloses a system for the preparation of methanol comprising two reaction units, wherein a first unit is operated on a mixture of fresh synthesis gas and unconverted synthesis gas and a second unit solely with unconverted synthesis gas. The fresh inlet syngas is mixed with a recycled one and fed to a first reactor. The products are condensed, and the unreacted gases are part recycled back with a compressor to the first reactor and the other part is fed to a second reactor. From this second reactor, the products are condensed, and the unreacted gas is recycled back to the first reactor.

U.S. Pat. No. 3,475,136 A discloses an apparatus for effecting exothermic gaseous reactions at elevated temperatures and pressures in the presence of a subdivided contact material which must from time to time be withdrawn from the apparatus and replaced with a fresh charge of contact material. The apparatus includes an external pressure shell and internals including supports for the contact material, baffles and conduits for gaseous reactants and products and conduit through which the contact material may be withdrawn and replaced, the foregoing being of a size and design which permits inspection of the internals and replacement of contact material without removal of the internals from the external pressure shell.

EP0448019A2 discloses a method for preparing methanol by reacting synthesis gas comprising hydrogen and carbon oxides ($CO$, $CO_2$) in a fixed bed methanol synthesis catalyst, the improvement comprises reacting the synthesis gas at reaction conditions, where condensation of methanol occurs on the catalyst.

EP0026057A1 discloses a reactor system for catalytic gas reactions such as synthesis of methanol or ammonia comprising at least one cylindrical catalyst bed having a height not greater than half its over-all diameter and defined on its underside by a grid supported by a dished plate having peripherical mechanical connection to a downward extension of the bed wall. Preferably there are several such beds and indirect heat exchanger upstream of the downstream-most bed.

Alternatives are explored to the conventional systems and methods described in the prior art, in order to avoid the recycle gas stream which introduces a recycle compressor (not cheap machine) and oversize all the reaction loop because the inlet to recycle flow is 1 to 4/5.

SUMMARY OF INVENTION

A solution to the problems of the state of the art is to shift the reaction balance towards methanol generation and improve the reaction performances (CO and $CO_2$ to methanol) via removing the products of reaction (methanol and water) from the reactor.

The present invention is related to a system for methanol production from a synthesis gas rich in hydrogen and $CO_2$/CO based on removing the reaction products via condensation. Once removed, the reaction continues in a second reaction step. Several reaction and removing product via condensation steps are connected in series.

The system for methanol synthesis from a synthesis gas rich in hydrogen and $CO_2$/CO comprises:
- a first adiabatic reactor arranged vertically in a cylindrical envelope, the first adiabatic reactor with a structure comprising an inlet stream joined to a first catalytic bed, one Venturi type mixing element next to and connected to the first catalytic bed, a first divergent nozzle next to and connected to the Venturi type mixing element which is arranged to receive a mix of reactants and products from the first catalytic bed, quench it and feed to a second catalytic bed located next to and connected to the divergent nozzle and one outlet stream leaving from the second catalytic bed;
- a first heat exchanger connected to the outlet stream downstream the reactor, the first heat exchanger being arranged to receive the stream exiting the second catalytic bed;
- a condenser connected to the heat exchanger downstream the heat exchanger, the condenser being arranged to receive a cooled stream of methanol and reactants exiting from the first heat exchanger;
- a separator connected to the condenser downstream the condenser, the separator being arranged to receive a stream exiting from the condenser, separate reactants from products and feed the reactants as quench to Venturi type mixing element and the first heat exchanger;
- a first cold gas stream joining the separator to both the first heat exchanger and the first Venturi type mixing element;
- a first outlet stream joining the heat exchanger to a second adiabatic reactor;
- The second adiabatic reactor is arranged vertically in a cylindrical envelope, the second adiabatic reactor comprises a structure receiving the first outlet stream, an additional catalytic bed, an additional Venturi type mixing element next to and connected to the additional catalytic bed, an additional divergent nozzle next to and connected to the additional Venturi type mixing element which is arranged to receive a mix of reactants and products from the additional catalytic bed, quench it and feed to a second additional catalytic bed located next to and connected to the additional divergent nozzle and an additional outlet stream leaving the second additional catalytic bed;

The system further comprises an additional heat exchanger connected to the additional outlet stream downstream the second adiabatic reactor, the additional heat exchanger being arranged to receive the stream exiting the second additional catalytic bed; an additional condenser connected to the additional heat exchanger downstream the additional heat exchanger; the additional condenser being arranged to receive a cooled stream of methanol and reactants exiting from the additional heat exchanger; an additional separator connected to the additional condenser downstream the additional condenser, the additional separator being arranged to receive a stream exiting from the additional condenser, separate reactants from products and feed the reactants as quench to additional Venturi type mixing element and the additional heat exchanger; an additional cold gas stream joining the additional separator to both the additional heat exchanger and the additional Venturi type mixing element; and a second outlet stream leaving the second adiabatic reactor.

The system of the invention can further comprise a second heat exchanger located between the first heat exchanger and the condenser; a second cold gas stream joining the second heat exchanger to the first heat exchanger and to the second Venturi type mixing element.

The first adiabatic reactor further comprises a second Venturi type mixing element located downstream the second catalytic bed and next to a third catalytic bed, a second divergent nozzle next to the Venturi type mixing element and a third catalytic bed next to the divergent nozzle.

The system of the invention can further comprise a second additional heat exchanger located between the first additional heat exchanger and the additional condenser; and a second additional cold gas stream from the second additional heat exchanger to the first additional heat exchanger and the second additional Venturi type mixing element.

The second adiabatic reactor further comprises a second additional Venturi type mixing element, a second additional divergent nozzle and a third additional catalytic bed located downstream the second additional catalytic bed.

The system of the invention can further comprise a temperature controller connected to the first catalytic bed that generates information about the temperature of the first catalytic bed; and a valve configured to regulate a methanol inlet into the inlet stream according to the information received of the temperature controller.

In the system of the invention the first divergent nozzle and the additional divergent nozzle have an angle between 10° and 30°.

In the system of the invention the second divergent nozzle and the second additional divergent nozzle have an angle between 10° and 30°.

This system allows for a cheaper solution than the conventional one. It has more units connected in series than the conventional systems, but of much lower diameter, reducing drastically the material cost. Other important aspect is that it avoids the use of a compressor, with is an expensive machine.

The following advantages are envisaged regarding the current systems:
- Less cost of equipment: because only a fraction of unreacted reagents is recycled and strategically distributed in several points of the reactor embodiment (quenches), the size of reactor and pipes is significantly reduced (diameter), compared to the conventional process, in which the total amount of unreacted reagents is recycled to the feed, that increases its flowrate (flowrate in conventional reactors is about 4 times that of invention). On the other hand, every further reaction step is reduced in size, as the total feed to treat gets reduced in each stage. Finally, no compressor is required to recycle the reagents, as explained below in "less electricity consumption".
- The invention has even more economic advantages for small and medium scale methanol production due to the fact of avoiding the recycle compressor. For small units the cost weight of adding a compressor (even a small one) is higher than in large scale plants.
- Less cost of catalyst: compared to the conventional process and derived from the reduction of size of the reactors, the amount and hence cost of catalyst bed is reduced to about 60% of that of the conventional process.

More reliable (less complexity): the unit proposed is simpler that the conventional process because:

It has no rotative equipment inside (compressors) as explained below in "less cost of electricity". This translates in less probability of failures and loss of production.

The boiling water-steam circuit section is not required, so the reactor is simpler to be built and controlled. This translates in less probability of failures and loss of production, but as well in more safety compared to the conventional process, where a tube rupture is possible, mixing boiling water with chemical at high pressures, leading to potential mayor disasters.

Less electricity consumption: the quenches of unreacted reagents over the reactor are performed by venturi effect, in the transition throats between catalytic beds. The quenches would flow naturally without need of compressors, so the consumption of electricity for compression gets reduced compared to a conventional unit.

Turn down improved due to adiabatic fixed bed operation. Standard conventional multi-tubular reactors have turn downs near 50%. Going below this point could produce damage to the catalyst inside the refrigerated tubes because the thermal conduction due to convective fluid movement is drastically reduced, producing an undesirable temperature peak inside the tube. Using fixed bed adiabatic reactors allows for a wider rangeability. Operational flexibility is an appreciated fact in intermittent or nonlinear applications as power to methanol.

So in turn the total cost of a unit is envisaged to be reduced to near 50% of that of a conventional one.

There are differences between the present invention and U.S. Pat. No. 8,629,190B2.

In U.S. Pat. No. 8,629,190B2 the gas is reacted in a typical tubular reactor refrigerated, but the unreacted gas from the condensing separation is sent to a further reaction step. The products from this second reaction step are condensed and the unreacted gases are recycled again to the first reactor with a recycle compressor. The system is a variance of the conventional one but with two reaction steps in the reaction loop. The present invention has the advantage of not using a recycle compressor. The stream that flows through the reactors is much lower in the present invention providing smaller diameter sized equipment resulting in more cheap solution. Also, the adiabatic design allows for cheaper construction reactors over standard multi-tube design.

There are differences between the present invention and EP0483919A2 and U.S. Pat. No. 5,216,034A. In these patents several fluidized bed reactors are arranged in series with product condensation and separation in between. These fluidized bed reactors are also cooled. A fluidized bed reactor represents a bigger size with respect the adiabatic piston flow fixed bed reactor. If they have a cooling system, the reactor is more complex. They operate in a constant homogeneous temperature since the solid catalyst is moving but the gas phase composition has multiple dispersion effects, resulting in a bigger size reactor. Also, one advantage of the adiabatic piston flow fixed bed reactor is that as long as reaction proceeds, temperature growths along the reactor, increasing in turn the reaction velocity or quicker kinetics until equilibrium is reached. Operating in a single intermediate temperature provides slower kinetics. Including quenches with free of products cool gas after each adiabatic reaction fixed bed represents a more compact, especially in diameter, reactor design, and cheaper. Fluidized bed reactor turn-down ratio is low, they are not very flexible in operation.

There are differences between the present invention and U.S. Pat. No. 5,262,443A. In this patent a system for preparing methanol by reacting synthesis gas comprising hydrogen and carbon oxides in a fixed bed of methanol synthesis catalyst is disclosed. The reaction of the synthesis gas is conducted under conditions where condensation of methanol occurs on the catalyst. This represents a different approach as condensation happens together with reaction. The required higher pressure to perform this condensation at reaction temperatures than the present invention, resulting in more wall thickness of the vessels and more initial compression energy given to the feed syngas. Also, standard methanol synthesis catalyst is deactivated if water is condensed in liquid state and are not active below 200° C. Liquid water is normally a poison. Water is a normal product, together with methanol, if $CO_2$ is present in the feed gas. In the present invention, as condensation is prevented to happen in the catalyst, a conventional catalyst could be used. In U.S. Pat. No. 5,262,443A, a special catalyst shall be used to avoid deactivation, increasing the price. Probably some recycling with a compressor is still needed to increase the overall conversion.

There are differences between the present invention and U.S. Pat. No. 6,881,759B2. Said patent describes a process for methanol production in a liquid phase reactor from synthesis gas. The liquid phase reactor contains a solid catalyst suspended in methanol. The methanol acts both as a product and as a suspension medium for the catalyst. It exploits the condensing conditions for methanol production. This is a very different system compared with the present invention. Some recycling with a compressor is still needed to increase the overall conversion, as indicated in the patent. The required higher pressure to perform this condensation at reaction temperatures than the present invention, resulting in more wall thickness of the vessels and more initial compression energy given to the feed syngas.

There are differences between the present invention and EP2626129A1. Said patent discloses an invention of a multiple reaction set to produce chemicals by equilibrium limited reactions utilizing plate-type or extended surface heat ex-changers. The heat exchangers effectively cool the reaction products to condense the methanol contained within the reaction products for separation, and also to warm incoming feed reactants prior to entrance of the reactants into a reactor utilized for the production of methanol. In the present invention, a quench is performed with cool gas free of products after a catalytic reaction stage. This allows for extending the reaction extent in the same reactor going thought a further catalytic bed. The system is much efficient than the patents (only one reaction step between product separation) indicated and of easier constructability, due to its simplicity.

There are differences between the present invention and EP0988267B1. This patent describes a system, including the synthesis gas production stage. The patent is focused in the reformer for synthesis gas production. However, it has a common methanol synthesis gas loop without compressor. The patent indicates that several reaction steps could be connected with methanol separation between them. Also, the reactor has multiple tubes, in this case with a coolant flow inside the tubes.

The present invention has several reaction stages in each reactor with quenchers between reaction catalytic beds using cool unreacted separated gas free of products in venturi-mixers. The present invention is based in adiabatic fixed bed reactor type, more compact than multi-tube refrigerated reactors and cheaper. Also, the heat integration between reaction arrangements or stages is not described in the patent. In the present invention this problem is solved and described, not resulting in additional heat consumption.

There are differences between the present invention and WO2017025272A1.

The method the adiabatic temperature is controlled it is quite different. In WO 2017025272A1 the bed is sub-sized for nominal flow in order to limit the reaction extent and for partial load a controlled recycle is envisaged. In the present invention a methanol injection to the inlet stream is controlled in order to limit the maximum temperature, adjusting the equilibrium conversion point.

WO2017025272A1 considers an inlet flow with impurities, having the cleaning step included inside the process. In the present invention a clean syngas is considered, limiting the scope of the system. Recycling with a compressor is needed to increase the overall conversion, as indicated in the patent, in the present invention no gas recycle compressor is used, putting more than one reactor unit in series, providing a more robust solution. In this document the main synthesis reactor type is open, could be adiabatic multistage with quenches in between, could be multi-tubular, etc. Compared to the multistage adiabatic, the present invention has special venturi devices that avoid recycle compressor, the diverging nozzle angle is critical for proper quench gas recycle. The quenching method of the present invention has the advantage that no control is envisaged for each gas quench as it will suction a recycle flow as a basis on the unit load, resulting on a pressure profile along the venturi throat, eliminating the use of control valves and recycle compressor.

There are differences between the present invention and U.S. Pat. No. 5,173,513.

In this patent the amount of recycle gas is less than in a conventional unit as part of it is enriched in hydrogen via separating $CO_2$. This in turn implies WGS reactors and PSA (Pressure Swing Absorption) units. Recycling with a compressor is still needed to increase the overall conversion, as indicated in the patent, in the present invention no gas recycle compressor is used, putting more than one reactor unit in series, providing a more robust solution. In U.S. Pat. No. 5,173,513, when using adiabatic reactors, a method for proper temperature control is needed, which will be required as result of rich CO gas ($CO_2$ is captured). It is indicated to reduce the operating pressure to control this temperature, as it will limit also the equilibrium maximum reaction extent and thus the temperature. Continuous pressurizing and depressurizing of a unit could result in vessel fatigue. Introducing methanol, as in the present invention, represents a much faster and accurate method for temperature control. Compared to the multistage adiabatic, the present invention has special venturi devices that avoid recycle compressor, the diverging nozzle angle is critical for proper quench gas recycle. The quenching method of the present invention has the advantage that no control is envisaged for each gas quench as it will suction a recycle flow as a basis on the unit load, resulting on a pressure profile along the venturi throat, eliminating the use of control valves and recycle compressor.

There are differences between the present invention and MX2015000667A.

In this patent it is not specified the reactor type to be used and is open. It does not cover means for adiabatic reactor temperature control, or how to cool down in the quenches between reaction stages. In the present invention solutions to these problems are indicated. Recycling with a compressor is needed to increase the overall conversion, as indicated in the patent, in the present invention no gas recycle compressor is used, putting more than one reactor unit in series, providing a more robust solution.

There are differences between the present invention and U.S. Pat. No. 3,475,136A.

In this patent the main reference is the ammonia synthesis reactor with different embodiments. Although clear application in ammonia synthesis it does not exclude methanol synthesis. These types of reactors are used when high pressure together with high temperature are met. The key issue is to provide a cheaper solution via reducing the design temperature of the outer shell that withstands the high pressure. The cold gases are in contact with the outer pressure shell while the hot reaction gases in contact with the catalyst are located inside with low design pressure (only pressure drop in the unit). Methanol synthesis is a high-pressure application but not high temperature. Between the reaction stages, located inside of the apparatus, quenches with cold gas are done in order to cool down the reaction gases from a catalyst bed in order to continue reaction in a further stage. These quenches, which could have the shape of a venture as described in the patent, have the aim of cooling down and mix. In the present invention the venture quenches have a further aim that is to allow for gas recycle. In this case a special venture design, with a diverging nozzle angle between 10° and 30° is needed, representing a different scenario and purpose.

There are differences between EP0448019A2 and the present invention. In this patent the reactor is working in certain thermodynamic conditions where the condensation of the products could take place. In the present invention the reactor is always working in gas phase. In said patent it is used a syngas rich in CO and very poor in $CO_2$, this implies that methanol is the only product. If some $CO_2$ is present in the syngas (normal situation), water will be also a product (through reaction (1)) and the stability of the catalyst with condensed water could be compromised.

In EP0448019A2 it is recycled the reaction liquid product, in the cases studied with only methanol, to the inlet in order to control the adiabatic temperature (in case an adiabatic reactor is used). This situation is only valid if the syngas is very rich in CO and has no $CO_2$, which represents a special case. Working with syngas with $CO_2$ will produce methanol and water as products. If these condensed products are recycled for temperature control, water will produce the WGS reaction (through reaction (3)) that is exothermic, and no efficient way of controlling the adiabatic temperature is achieved. In the present invention, it is used pure methanol of high quality, with very low amount of water, that could be taken from a downstream distillation process. Then it allows for proper adiabatic temperature control that allows working with any syngas composition, not limited to very low amount of $CO_2$.

There are differences between the present invention and EP0026057A1.

This patent is focused on reactor design to overcome the state of the art limitations for big units, the support of the catalytic bed and the mixing system. In this patent the reference is for methanol and ammonia synthesis reactor. The double shell type of reactors are used when high pressure together with high temperature are met. In one of the embodiments a cheaper solution via reducing the design temperature of the outer shell that withstands the high pressure is discussed. The cold gases are in contact with the outer pressure shell while the hot reaction gases in contact with the catalyst are located inside with low design pressure (only pressure drop in the unit). Methanol synthesis is a high-pressure application but not high temperature so this double shell embodiment is not needed. Between the reaction stages, located inside of the apparatus, quenches with cold gas are done in order to cool down the reaction gases from a catalyst bed in order to continue reaction in a further stage. These quenches, are made in gas mixing zones with spargers, with the purpose to cool down and mix. In the present invention the quenches are done using venturi element that have a further aim that is to allow for gas recycle. In this case a special venturi design, with a diverging nozzle angle between 10° and 30° is needed, representing a different scenario and purpose.

It does not cover means for adiabatic bed temperature control, only for quenches. Controlling the bed maximum temperature with the quench is not possible as normally, the methanol synthesis catalysts are not active below 200° C.

In the present invention a methanol injection to the inlet stream is controlled in order to limit the maximum bed temperature, adjusting the equilibrium conversion point.

Recycling with a compressor is needed to increase the overall conversion and provide the cold gas to perform the quench, as indicated in the patent. In the present invention no gas recycle compressor is used, putting more than one reactor unit in series, providing a more robust solution.

The quenching method of the present invention has the advantage that no control element is envisaged for each gas quench as it will suction a recycle flow as a basis on the unit load, resulting on a pressure profile along the venturi throat, eliminating the use of control valves and recycle compressor.

LIST OF REFERENCE NUMERALS

Figure 1:
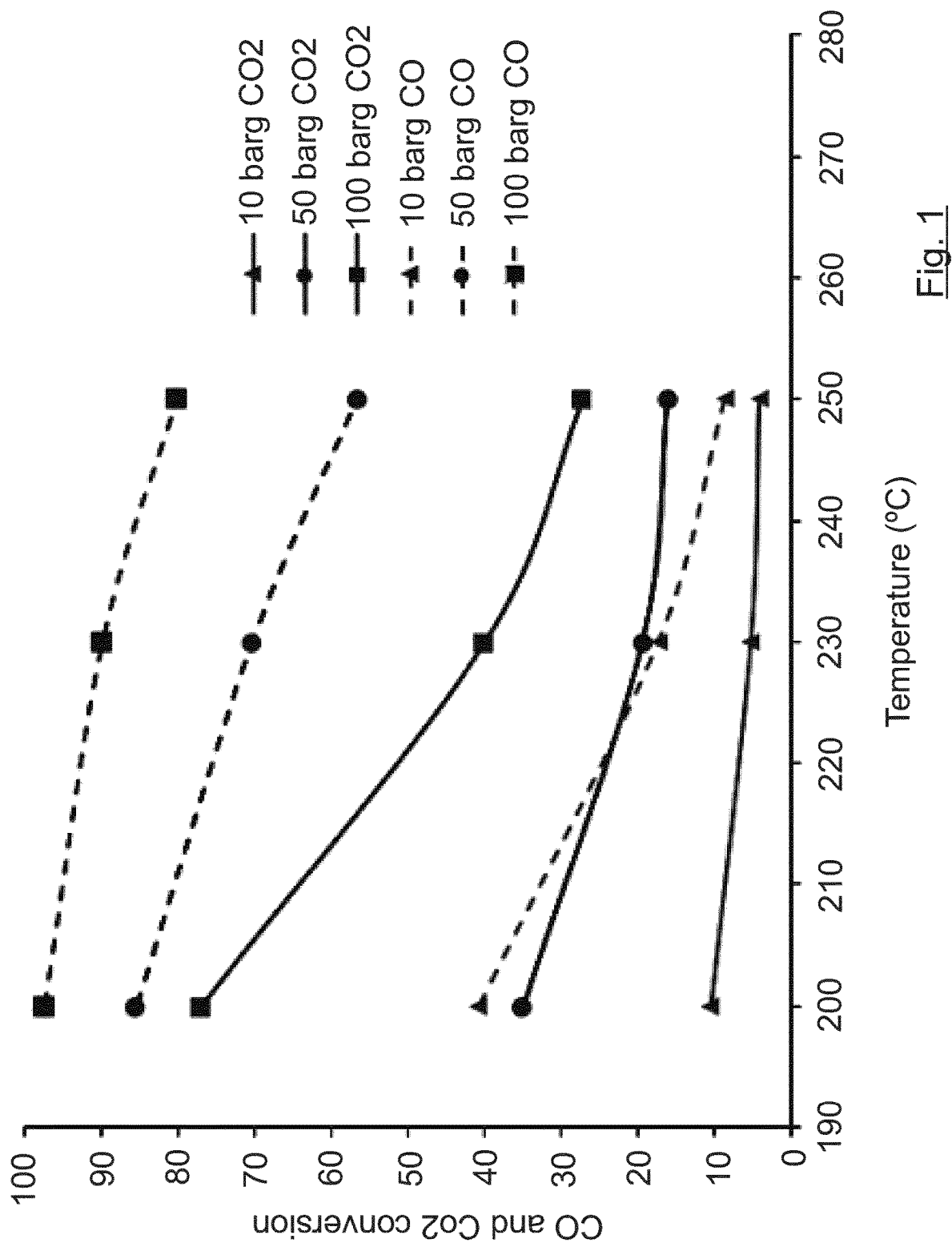
FIG. 1 shows the equilibrium conversion for CO and $CO_2$ with temperature at different pressures.

10 Inlet/Feed stream
11 First adiabatic reactor
12 First catalytic bed
13 First Venturi type mixing element
14 First divergent nozzle
15 First heat exchanger
16 Condenser
17 Cooling water or air
18 Separator
19 First cold gas stream
20 Crude methanol
21 First outlet stream
22 Second cold gas stream
23 Second heat exchanger
24 Second adiabatic reactor
25 Second outlet stream
26 Cylindrical envelope
27 Second catalytic bed
28 Outlet stream
29 Third catalytic bed
30 Second Venturi type mixing element
31 Second divergent nozzle
32 Temperature controller
33 Valve
34 Additional catalytic bed
35 Additional Venturi type mixing element
36 Additional divergent nozzle
37 Additional cold gas stream
38 Second additional catalytic bed
39 Additional outlet stream
40 Additional heat exchanger
41 Additional condenser
42 Additional separator
43 Second additional type mixing element
44 Second additional divergent nozzle
45 Third additional catalytic bed
46 Second additional heat exchanger
47 Second additional cold gas stream

DESCRIPTION OF EMBODIMENTS

Figure 2:
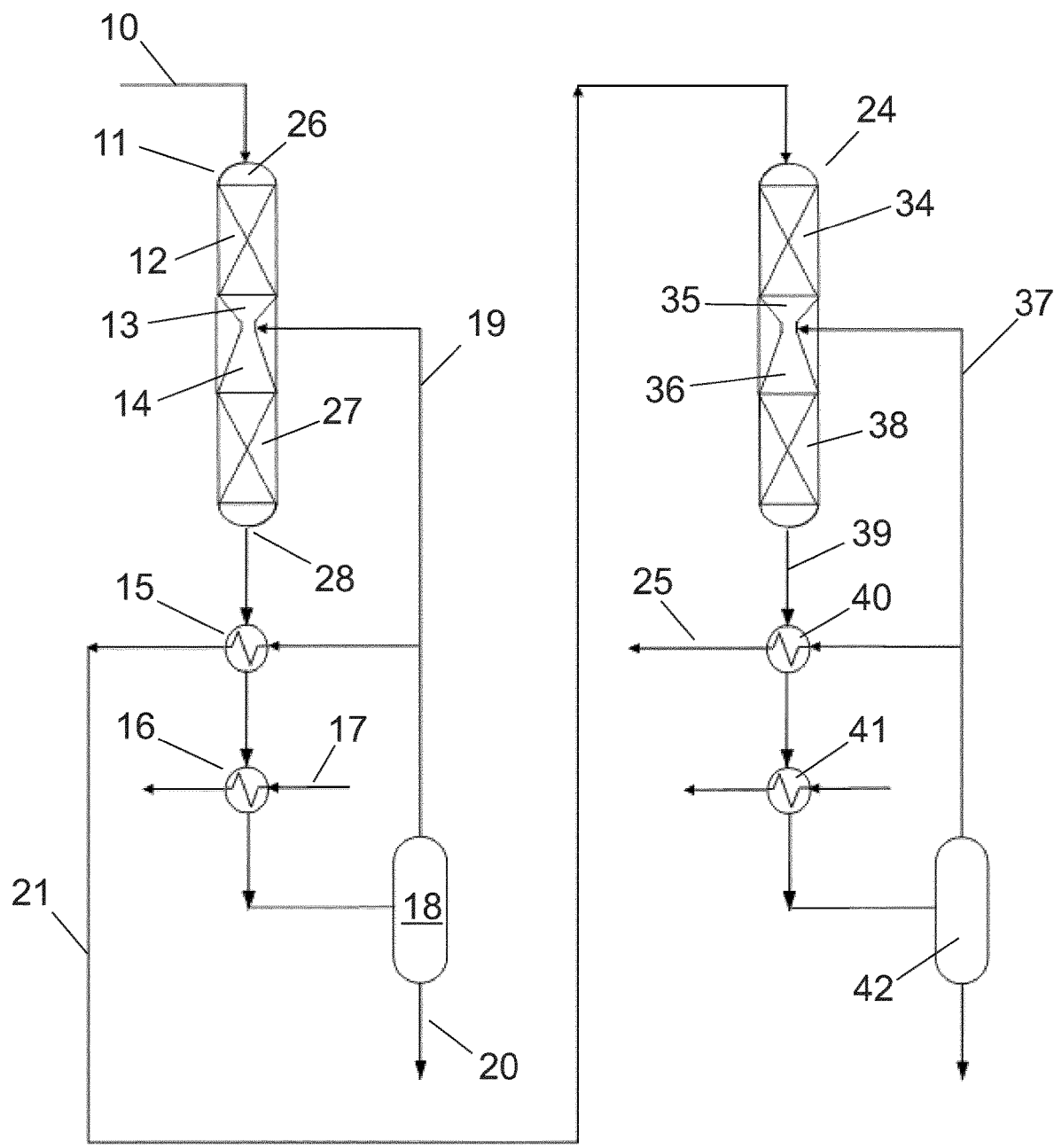
FIG. 2 shows a first embodiment of methanol synthesis system.

The first embodiment (FIG. 2) describes a system for methanol synthesis from a synthesis gas rich in hydrogen and $CO_2$/CO that comprises the following elements.

A first adiabatic reactor (11) designed as an adiabatic reactor with a cylindrical envelope (26) disposed in a vertical arrangement. The gas flow pattern is through the cylinder envelope (26) going downwards. The first adiabatic reactor (11) is constructed with a metal alloy.

In a first embodiment (shown in FIG. 2) of the invention, a system for methanol synthesis from a synthesis gas rich in hydrogen and $CO_2$/CO comprises:

the first adiabatic reactor (11) with a structure comprising one inlet stream (10) joined to a first catalytic bed (12), one Venturi type mixing element (13) next to and connected to the first catalytic bed (12), a first divergent nozzle (14) with an angle between 10° and 30° next to and connected to the Venturi type mixing element (13), a second catalytic bed (27) next to and connected to the first divergent nozzle (14) and one outlet stream (28) exiting from the second catalytic bed (27);

a first heat exchanger (15) positioned downstream the reactor (11) on the outlet stream (28);

a condenser (16) located downstream and connected to the heat exchanger (15);

a separator (18) positioned downstream the condenser (16) connected through a first cold gas stream (19) to the first heat exchanger (15) and to the first Venturi type mixing element (13);

a first outlet stream (21) exiting from the heat exchanger (15) reaching a second adiabatic reactor (24);

the second adiabatic reactor (24) is identical to the first adiabatic reactor (11) and is located between a second outlet stream (25) and the first outlet stream (21); and the second outlet stream (25) exiting from the second adiabatic reactor (24) going to a boiler or to a further adiabatic reactor.

The first catalytic bed (12) is located inside the envelope (26). The reagents perform several reactions to reach an outlet composition near the equilibrium, increasing the temperature. The temperature of the inlet stream (10) is controlled in order to keep the maximum temperature in the first catalytic bed (12) below a safety maximum (mainly for catalyst stability). Provisions for proper catalytic bed temperature monitoring are to be provided.

The Venturi type mixing element (13) which acts as a quench element where the first cold gas stream (19) free of reaction products (methanol and water) is taken and mixed with the outlet gas from the first catalytic bed (12). In order to avoid a recycle compressor, this quench is done in a venturi throat located between each catalytic bed (12, 27). This quench is performed without compressor to the lowest pressure zone of the first Venturi type mixing element (13) located in the throat. It has two beneficial effects: one of them is to increase the reagents concentration in order to misbalance the equilibrium towards products; other is to cool down the outlet from the first catalytic bed (12) to a temperature where the equilibrium is misbalanced again (between 200 and 250° C.).

The specially designed venturi allows for gas recycling because of lower pressure located in the throat produced by gas acceleration to higher velocities. The venturi will only work if the first diverging nozzle (14) downstream pressure is higher than the pressure on the throat. The angle of the first diverging nozzle (14) determines most of the total pressure drop of the Venturi type mixing element (13). Angles bigger than 45° are not suitable since the pressure of the outlet is even lower than the pressure in the throat, therefore is not possible to recycle the gas.

It is observed that when the angle of the a first divergent nozzle (14) is approximately 30°, the outlet pressure is higher than the throat pressure, this is because the pressure drop in diverging nozzle is reduced and the Bernoulli Effect of decelerating the gas from the throat high velocity to the diverging nozzle outlet diameter low velocity has more weight.

The venturi throat smoothly increases the diameter (first divergent nozzle 14) to recover the pressure and keep pressure losses in the venturi to a minimum. In the present invention, the first diverging nozzle (14) has an angle smooth enough to recover great part of the pressure loss. The angle of said diverging nozzle is between 10° and 30°, more preferably between 25° and 15°, to keep pressure losses to a minimum and in order to allow recycling the cold gas to the throat, acting as a quench and as a "low cost" recycle, avoiding the use of a recycle compressor.

The first heat exchanger (15) reduces the outlet temperature of the reaction products from the first adiabatic reactor (11), increasing in turn the temperature of the gas stream from the separator (18) up to 200° C. to 250° C. This heat integration has several advantages: reducing the amount and cost of cooling water or air to condense the products (methanol and water) and heating the gas segregated from liquid in the separator (18) to the required reaction temperature for further conversion.

The second adiabatic reactor (24) is arranged vertically in a cylindrical envelope, the second adiabatic reactor (24) comprises a structure receiving the first outlet stream (21) an additional catalytic bed (34), an additional Venturi type mixing element (35) next to and connected to the additional catalytic bed (34), an additional divergent nozzle (36) next to and connected to the additional Venturi type mixing element (35), a second additional catalytic bed (38) next to and connected to the additional divergent nozzle (36) and an additional outlet stream (39) leaving the second additional catalytic bed (38).

The additional outlet stream (39) of the second adiabatic reactor is connected to an additional heat exchanger (40) which is in turn connected to an additional condenser (41) downstream the additional heat exchanger (40); and the additional condenser (41) is connected to an additional separator (42) downstream the additional condenser (41). An additional cold gas stream (37) joins the additional separator (42) to both the additional heat exchanger (40) and the additional Venturi type mixing element (35).

Figure 3:
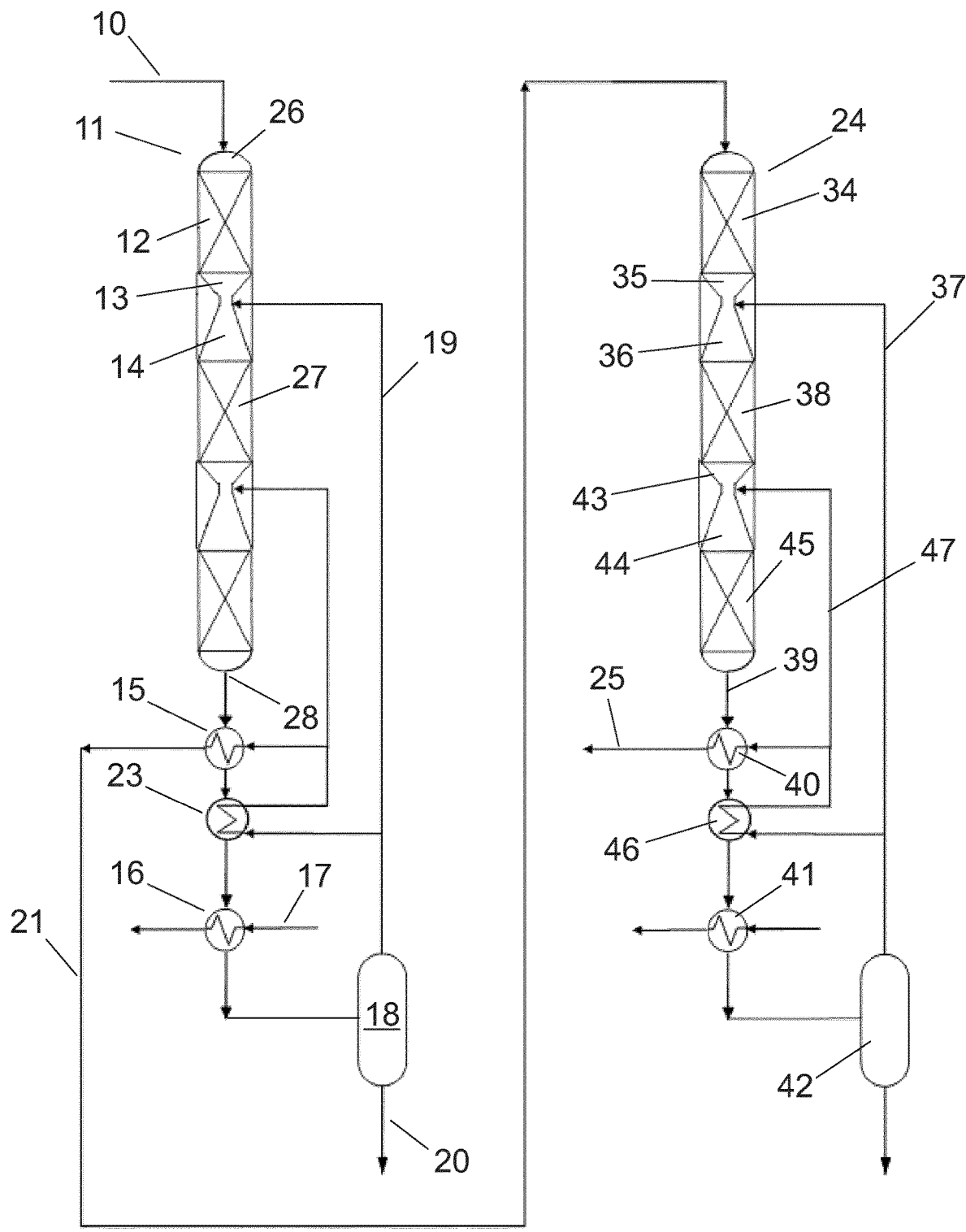
FIG. 3 shows a second embodiment of methanol synthesis system.

A second embodiment (as seen in FIG. 3) of the system of the invention comprises the elements of the first embodiment, and it further comprises:
    a second heat exchanger (23) located between the first heat exchanger (15) and the condenser (16);
    a second cold gas stream (22) from the second heat exchanger (23) to the first heat exchanger (15) and the second Venturi type mixing element (30); and
    wherein the first adiabatic reactor (11) further comprises a second Venturi type mixing element (30) located downstream the second catalytic bed (27) and next to a third catalytic bed (29), a second divergent nozzle (31) with an angle between 10° and 30° next to the Venturi type mixing element (30) and a third catalytic bed (29) next to the divergent nozzle (31).

The second embodiment (as seen in FIG. 3) describes a system for methanol synthesis process similar to the system of the first embodiment described previously but some differences are evidenced.

The first adiabatic reactor in the second embodiment further comprises:
    a second type mixing element (30), a second divergent nozzle (31) and a third catalytic bed (29) located downstream the second catalytic bed (27) can be found;
    a second heat exchanger (23) located between the first heat exchanger (15) and the condenser (16) can be found; and
    a second cold gas stream (22) from the second heat exchanger (23) to the first heat exchanger (15) and the second Venturi type mixing element (30) can be found.

The second adiabatic reactor (24) in the second embodiment further comprises:
    a second additional type mixing element (43), a second additional divergent nozzle (44) and a third additional catalytic bed (45) located downstream the second additional catalytic bed (38) can be found;
    a second additional heat exchanger (46) located between the first additional heat exchanger (40) and the additional condenser (41) can be found; and
    a second additional cold gas stream (47) from the second additional heat exchanger (46) to the first additional heat exchanger (40) and the second additional Venturi type mixing element (43) can be found.

In the first embodiment and in the second embodiment of the system of the invention, a second outlet stream (25) exiting from the second adiabatic reactor (24) could be routed to an additional adiabatic reactor, identical to the first adiabatic reactor (11) and to the second adiabatic reactor (24), or to a boiler.

The present invention provides an improved solution and is based in the condensation and separation of products (methanol and water) in several steps. Furthermore, the design is based on adiabatic and plug flow fixed bed reactor design, (no heat exchange to outside or another fluid), with catalyst inside. Flow pattern is downwards.

This design is much cheaper (manufacturing and less construction materials used) than typical multi-tube reactor. Other advantage is that the catalyst could occupy all the cylindrical section of the reactor, giving a more compact (much less diameter) reactor design for the same processing capacity/catalyst load than the multi-tube reactor, which only has catalyst inside the tubes.

On the other hand, one key issue of the multi-tube reactor is that the tubes and then the reaction, is refrigerated from the shell side, so the extent of reaction is higher as more equilibrium conversion could be achieved.

To overcome this potential limitation of the adiabatic reactor, the outlet of an adiabatic catalytic bed is quenched with cold gas and routed to other catalytic bed. The reduction in temperature allows for the reaction to continue in the next bed. Furthermore, this quench is done with cold gas with only reactive present, limiting the presence of products. This increases the reactants or reagents concentration, so the equilibrium is favored towards products. This cold gas could be taken from the separation of the condensing step downstream of each reactor in which via condensation the products are separated.

In the present invention, more than one reactor could be place in series with condensation separation between them. Each of the reactors shall have more than one catalytic bed separated by a venturi throat in which a quench is done with the gas free of products from the condensation step, which removes methanol and water by condensation.

Figure 4:
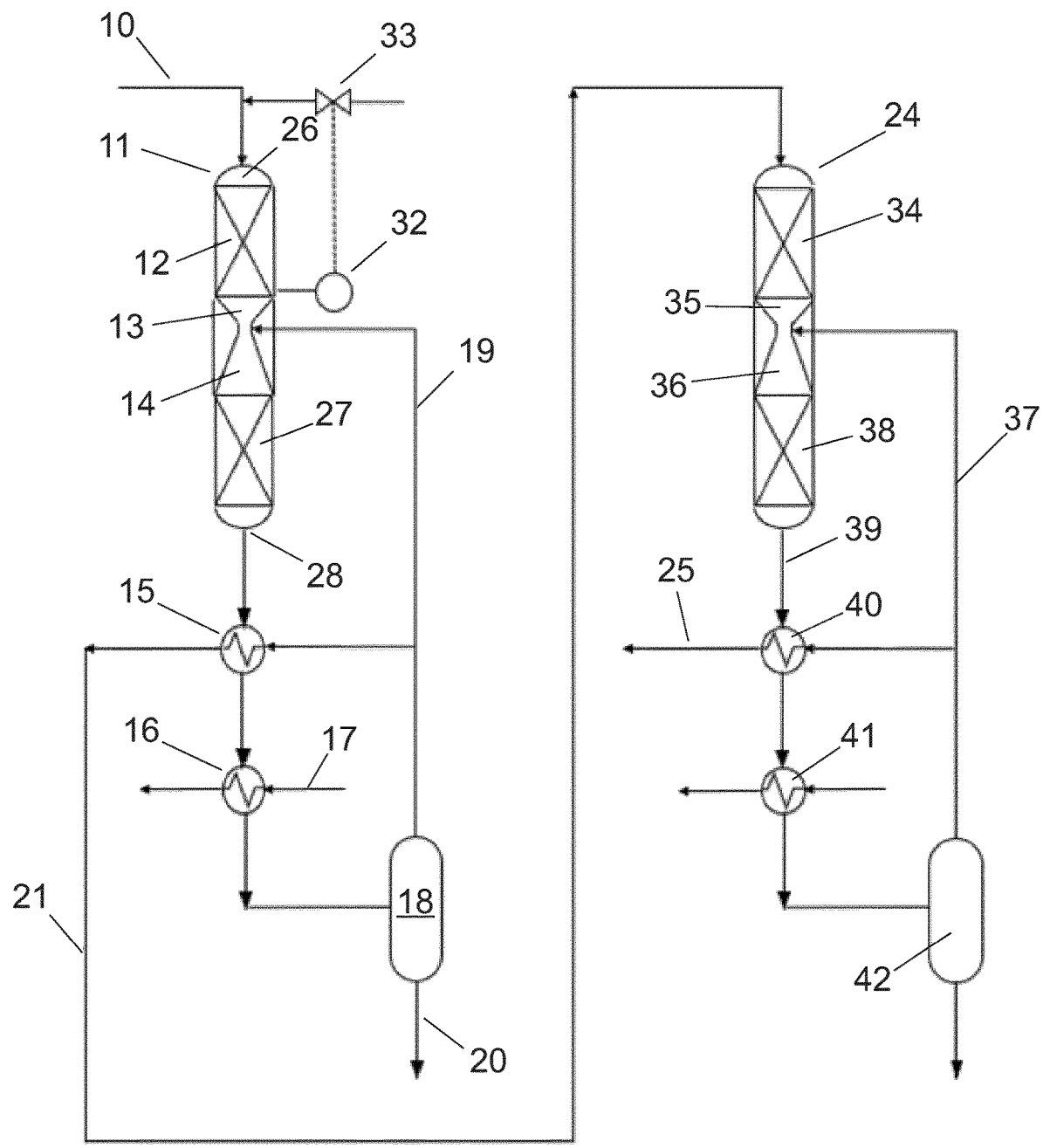
FIG. 4 shows a third embodiment of methanol synthesis system.

A third embodiment (shown in FIG. 4) of the system of the invention comprises the elements of the first embodiment, and it further comprises:
- a temperature controller (32) connected to the catalytic bed (12) that generates information about the temperature of the catalytic bed (12); and
- a valve (33) configured to regulate a pure methanol inlet into the inlet stream (10) according to the information received of the temperature controller (32).

The system disclosed in the third embodiment is similar to the system of first embodiment but with a temperature controller (32) connected to the adiabatic catalytic bed (12) that generates information about the temperature of the catalytic bed (12) and that regulates a pure methanol inlet flow (of certain high quality), that is mixed with the inlet stream (10), through a valve (33). This allows for temperature control via displacing the equilibrium conversion.

The adiabatic reactor reaches the equilibrium conversion as the temperature increases with the reaction extents along with catalytic bed height. As the outlet temperature of the adiabatic reactor is higher, the conversion is lower, but kinetics is faster. The outlet temperature of the adiabatic catalytic bed is controlled not to exceed 300° C. via injecting methanol in the inlet, limiting the equilibrium conversion.

If the syngas to be converted is rich in CO, the exothermicity of the reactions could produce the adiabatic temperature to exceed 300° C. This is a problem of an adiabatic fixed bed reactor because operating over 300° C. with commercial catalyst will produce some sintering in the catalyst and deactivation. Also, the selectivity towards other products different than methanol is increased. To overcome this limitation, the system includes a valve (33) configured to control a methanol inlet. The methanol inlet is mixed with inlet stream (10).

A temperature controller (32) connected to the adiabatic catalytic bed (12) regulates the methanol inlet flow through the valve (33). Via introducing pure methanol (it is necessary that the methanol has high purity), the equilibrium composition is controlled, limiting the reaction extent and thus the maximum temperature. This represents a better alternative to convert CO into $CO_2$ in WGS reactors upstream methanol synthesis process, as it could take advantage of the fast kinetics of CO compared to $CO_2$, representing a cheaper solution.

Figure 5:
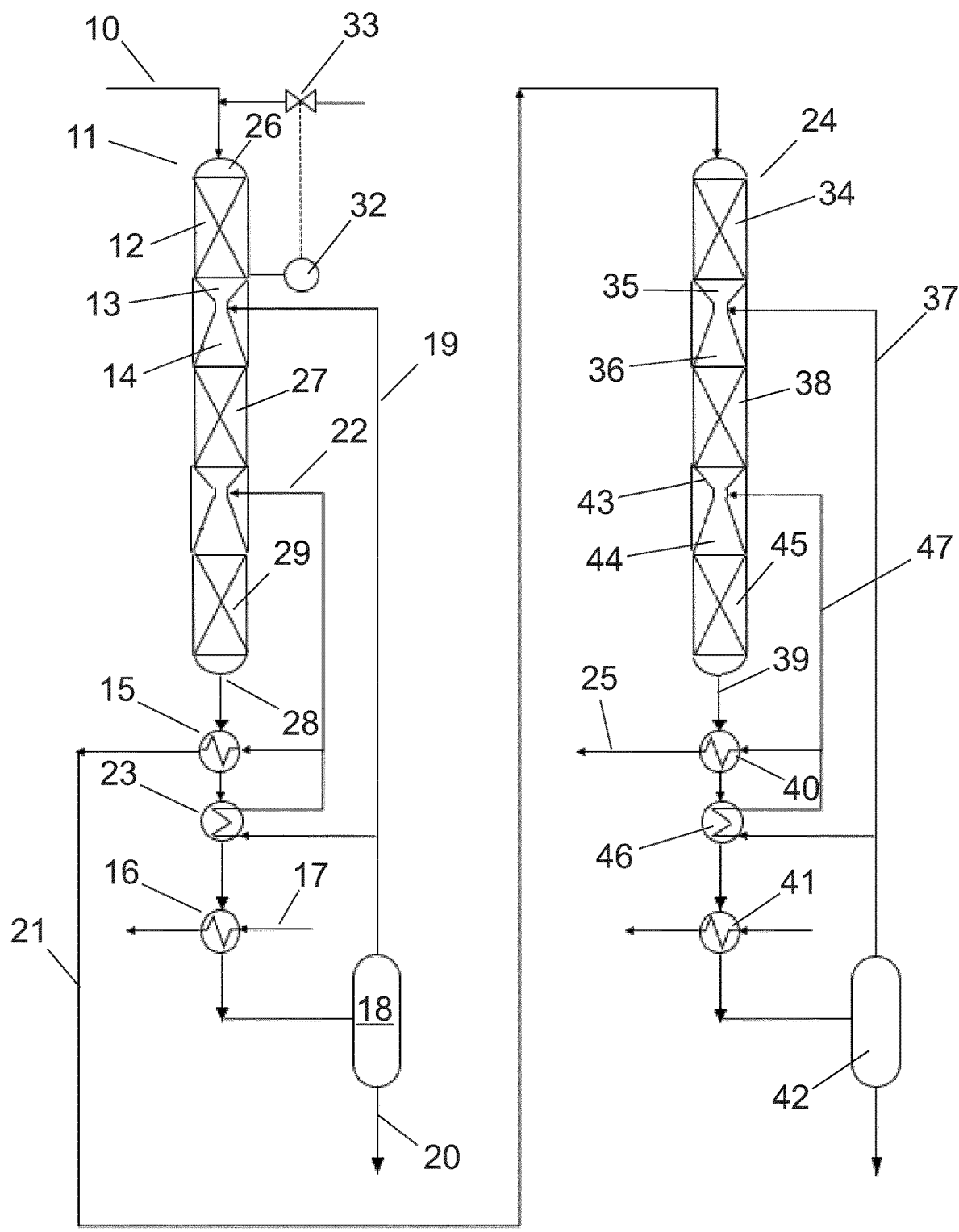
FIG. 5 shows a fourth embodiment of methanol synthesis system.

A fourth embodiment (shown in FIG. 5) of the system of the invention comprises the elements of the second embodiment and it further comprises:
- a temperature controller (32) connected to the catalytic bed (12) that generates information about the temperature of the catalytic bed (12); and
- a valve (33) configured to regulate a pure methanol inlet into the inlet stream (10) according to the information received of the temperature controller (32).

The fourth embodiment describes a system for methanol synthesis similar to the second embodiment described previously but with a temperature control system as described for the third embodiment.

The invention claimed is:

1. A system for methanol synthesis from a synthesis gas rich in hydrogen and $CO_2/CO$ comprising:
- a first adiabatic reactor (11) arranged vertically in a cylindrical envelope (26), the first adiabatic reactor (11) with a structure comprising an inlet stream (10) joined to a first catalytic bed (12), one Venturi type mixing element (13) next to and connected to the first catalytic bed (12), a first divergent nozzle (14) next to and connected to the Venturi type mixing element (13) which is arranged to receive a mix of reactants and products from the first catalytic bed, quench the reactants and products and feed to a second catalytic bed (27) located next to and connected to the divergent nozzle (14) and one outlet stream (28) leaving from the second catalytic bed (27);
- a first heat exchanger (15) connected to the outlet stream (28) downstream the reactor (11), the first heat exchanger (15) being arranged to receive the stream exiting the second catalytic bed (27);
- a condenser (16) connected to the heat exchanger (15) downstream of the heat exchanger (15), the condenser (16) being arranged to receive a cooled stream of methanol and reactants exiting from the first heat exchanger (15);
- a separator (18) connected to the condenser (16) downstream of the condenser (16), the separator (18) being arranged to receive a stream exiting from the condenser, separate reactants from products and feed the reactants as quench to Venturi type mixing element (13) and the first heat exchanger (15);
- a first cold gas stream (19) joining the separator (18) to both the first heat exchanger (15) and the first Venturi type mixing element (13);
- a first outlet stream (21) joining the heat exchanger (15) to a second adiabatic reactor (24);
- the second adiabatic reactor (24) is arranged vertically in a cylindrical envelope, the second adiabatic reactor (24) comprises a structure receiving the first outlet stream (21), an additional catalytic bed (34), an additional Venturi type mixing element (35) next to and connected to the additional catalytic bed (34), an additional divergent nozzle (36) next to and connected to the additional Venturi type mixing element (35) which is arranged to receive a mix of reactants and products from the additional catalytic bed (34), quench the reactants and products and feed to a second additional catalytic bed (38) located next to and connected to the additional divergent nozzle (36) and an additional outlet stream (39) leaving the second additional catalytic bed (38);
- an additional heat exchanger (40) connected to the additional outlet stream (39) downstream the second adiabatic reactor (24), the additional heat exchanger (40)

being arranged to receive the stream exiting the second additional catalytic bed (38);

an additional condenser (41) connected to the additional heat exchanger (40) downstream the additional heat exchanger (40); the additional condenser (41) being arranged to receive a cooled stream of methanol and reactants exiting from the additional heat exchanger (40);

an additional separator (42) connected to the additional condenser (41) downstream the additional condenser (41), the additional separator (42) being arranged to receive a stream exiting from the additional condenser (41), separate reactants from products and feed the reactants as quench to additional Venturi type mixing element (35) and the additional heat exchanger (40);

an additional cold gas stream (37) joining the additional separator (42) to both the additional heat exchanger (40) and the additional Venturi type mixing element (35); and a second outlet stream (25) leaving the second adiabatic reactor (24).

2. The system according to claim 1, further comprising:

a second heat exchanger (23) located between the first heat exchanger (15) and the condenser (16);

a second cold gas stream (22) joining the second heat exchanger (23) to the first heat exchanger (15) and to the second Venturi type mixing element (30); and wherein the first adiabatic reactor (11) further comprises a second Venturi type mixing element (30) located downstream the second catalytic bed (27) and next to a third catalytic bed (29), a second divergent nozzle (31) next to the Venturi type mixing element (30) and a third catalytic bed (29) next to the divergent nozzle (31), a second additional heat exchanger (46) located between the first additional heat exchanger (40) and the additional condenser (41); and a second additional cold gas stream (47) from the second additional heat exchanger (46) to the first additional heat exchanger (40) and the second additional Venturi type mixing element (43);

where the second adiabatic reactor further comprises a second additional Venturi type mixing element (43), a second additional divergent nozzle (44) and a third additional catalytic bed (45) located downstream the second additional catalytic bed (38).

3. The system according to claim 1, further comprising a temperature controller (32) connected to the first catalytic bed (12) that generates information about the temperature of the first catalytic bed (12); and a valve (33) configured to regulate a methanol inlet into the inlet stream (10) according to the information received of the temperature controller (32).

4. The system according to claim 1, wherein the first divergent nozzle (14) and the additional divergent nozzle (36) have an angle between 10° and 30°.

5. The system according to claim 1 wherein the second divergent nozzle (31) and the second additional divergent nozzle (44) have an angle between 10° and 30°.

* * * * *